(12) United States Patent
Xia et al.

(10) Patent No.: US 8,009,946 B2
(45) Date of Patent: Aug. 30, 2011

(54) FIBEROPTIC PATIENT HEALTH MULTI-PARAMETER MONITORING DEVICES AND SYSTEM

(75) Inventors: Hua Xia, Altamont, NY (US); David Michael Davenport, Niskayuna, NY (US); Daniel Francis Strauch, Mt. Airy, MD (US); Steven Mitchell Falk, Baltimore, MD (US); Mark Lyman Kelly, Wesley Chapel, FL (US); Marilyn Ruth Lapidus, Columbia, MD (US); Lynn Elizabeth Lynam, Bel Air, MD (US); Lawrence Guy Ten Eyck, Ellicott City, ND (US); Clayton Ming Young, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 84 days.

(21) Appl. No.: 12/011,319

(22) Filed: Jan. 22, 2008

(65) Prior Publication Data

US 2009/0185772 A1    Jul. 23, 2009

(51) Int. Cl.
*G02B 6/34* (2006.01)
*G02B 6/00* (2006.01)

(52) U.S. Cl. .......................................... 385/37; 385/13

(58) Field of Classification Search ................. 385/13, 385/37
See application file for complete search history.

(56) References Cited

U.S. PATENT DOCUMENTS

| | | | |
|---|---|---|---|
| 5,182,779 A * | 1/1993 | D'Agostino et al. ........... 385/13 |
| 5,241,300 A | 8/1993 | Buschmann .................. 340/573 |
| 5,828,059 A * | 10/1998 | Udd ........................ 250/227.18 |
| 6,004,639 A * | 12/1999 | Quigley et al. .............. 428/36.3 |
| 6,191,414 B1 * | 2/2001 | Ogle et al. ............... 250/227.14 |
| 6,361,299 B1 * | 3/2002 | Quigley et al. .............. 428/35.9 |
| 6,381,482 B1 * | 4/2002 | Jayaraman et al. ........... 600/388 |
| 6,498,652 B1 | 12/2002 | Varshneya et al. ............ 356/477 |
| 6,687,523 B1 * | 2/2004 | Jayaramen et al. ........... 600/388 |
| 6,706,348 B2 * | 3/2004 | Quigley et al. .............. 428/36.3 |
| 6,776,045 B2 * | 8/2004 | Fernald et al. .................. 73/705 |
| 6,816,266 B2 * | 11/2004 | Varshneya et al. ............ 356/477 |
| 7,004,911 B1 * | 2/2006 | Tu et al. ........................ 600/549 |
| 7,025,723 B1 | 4/2006 | Watson ......................... 600/304 |
| 7,154,081 B1 * | 12/2006 | Friedersdorf et al. ... 250/227.14 |
| 7,282,698 B2 * | 10/2007 | Childers .................. 250/227.14 |
| 2002/0119271 A1 * | 8/2002 | Quigley et al. .............. 428/36.9 |
| 2003/0095263 A1 * | 5/2003 | Varshneya et al. ............ 356/477 |
| 2004/0096614 A1 * | 5/2004 | Quigley et al. .............. 428/36.3 |
| 2007/0075225 A1 * | 4/2007 | Xia et al. ................. 250/227.14 |
| 2007/0284112 A1 * | 12/2007 | Magne et al. .................. 166/336 |
| 2007/0289741 A1 * | 12/2007 | Rambow .................. 166/250.01 |
| 2008/0047662 A1 * | 2/2008 | Dria et al. ..................... 156/249 |
| 2008/0285909 A1 * | 11/2008 | Younge et al. .................. 385/13 |
| 2009/0185772 A1 * | 7/2009 | Xia et al. ........................ 385/13 |

* cited by examiner

*Primary Examiner* — K. Cyrus Kianni
(74) *Attorney, Agent, or Firm* — Jason K. Klindtworth (57) ABSTRACT

A patient monitoring system includes a plurality of diffraction gratings integrated along the length of an optical fiber, wherein the optical fiber and each grating are together configured to alter either the effective refractive index or grating periodicity of the respective grating at its corresponding location along the fiber in response to at least one desired external stimulus.

20 Claims, 10 Drawing Sheets

FIBEROPTIC PATIENT HEALTH MULTI-PARAMETER MONITORING DEVICES AND SYSTEM

BACKGROUND

The invention relates generally to patient health monitoring, and more particularly to a multi-parameter fiberoptic monitoring system and devices for patient health monitoring.

Monitoring the microenvironment and/or physiological state of a neonate significantly below typical gestational age is labor intensive and potentially injurious, given the frailty of the patient and sensitivity to medical sensing devices considered harmless by an adult. Neonates are required to stay in an incubation chamber (incubator), which provides thermal and little acoustic protection from the outside environment. Performing checkups on the patient by medical staff is problematic since applying care effectively perturbs the environment by opening the incubator, manipulating the neonate, applying sensors or equipment to the skin, cleaning, and other duties necessary to maintain the care area. Certain activities raise the ambient noise level, disrupt the infant's thermal environment, interfere with the circadian rhythm, and generally reduce the quality of life, with potentially serious implication for the baby's future.

The application of adhesive skin electrodes, for example, to monitor vital signs of the neonate may result in tearing of the skin as the sensors are removed at a later time since the skin of the neonate is extremely soft and pliable and has not hardened compared to the skin of adults. The opening of the skin provides an avenue for infection and contributes to the discomfort since the tearing of the skin is quite painful.

Further, the application of sensors requiring adhesion to the skin is generally intrusive to the patient, increasing their level of discomfort. In some cases, this results in poor sensor readout if the adhesive gel loses tack, or if the patient unconsciously manipulates the sensor by probing with fingers, scratching, etc.

The electrical environment of a patient care area, especially in the presence of electrocautery, defibrillation, or MRI equipment, is potentially harsh. The RF noise or eddy currents resulting from this equipment can cause interference to non-optical based patient sensing equipment since the electromagnetic fields created from the interfering equipment causes electrical artifacts on the acquired sensor data.

Patient monitors, as commonly known in hospitals today, usually have one cable associated for each sensor. In a high acuity care environment, for example, 10 ECG sensors for heart activity, 1 sensor for surface temperature, and 1 sensor for blood oxygen saturation already result in 12 cables hanging from the patient. Although harmless, this is bothersome for clinician and results in slow interaction when caring for the patient. The slight delays incurred over an entire workshift for every patient interaction result in an appreciable loss of productivity on the part of the caregiver.

Patient instrumentation is oftentimes dedicated where it is designed to perform a series of specific tasks in a hospital environment. In other cases, instrumentation can perform arbitrary tasks provided that a module supporting that task is physically connected to the module. This is problematic since sensors used to monitor a parameter require specialized electronics tailored to the requirement. The care institution therefore must manage a plurality of devices, accessories, configurations, and modules to support an adequate level of care for the local population.

Additionally, the humidity in neonatal microenvironments is generally much higher than that of the outside ambient environment to maintain skin pliability. This is also a breeding ground for microbes which can seriously compromise the health of a neonate, whose immune systems are far from developed.

The foregoing problems have generally been addressed through monitoring the incubator environment using single-point sensors and heating the neonate with infrared radiation. Further, monitoring the neonate has been performed using standard monitoring equipment that employs body-worn sensors to capture physiological data. The above approach is problematic however, due to issues concerning, without limitation, 1) real-time, continuous monitoring of airborne and waterbourne pathogens related from operation of a humidifier to moisturize the environment, 2) distributed temperature sensing to characterize and control the thermal environment, and 3) a means to characterized the motor activity of the neonate to assess neurological function or dysfunction.

A need therefore exists for a patient health multi-parameter monitoring system and/or patient health multi-parameter monitoring devices to overcome the foregoing shortcomings associated with present patient health monitoring systems and devices.

BRIEF DESCRIPTION

According to one aspect of the invention, a fiberoptic monitoring system comprises:

at least one optical fiber or fiber braid having a predetermined length; and at least one diffraction grating integrated into a desired portion of the at least one optical fiber or fiber braid, the at least one optical fiber or fiber braid and the at least one diffraction grating configured together such that an effective refractive index of the at least one diffraction grating changes in tandem with at least one predetermined external stimulus.

According to another aspect of the invention, a fiberoptic sensor comprises at least one diffraction grating integrated into a desired portion of at least one optical fiber or fiber braid, such that either an effective refractive index or the grating's periodicity of the at least one diffraction grating changes in response to at least one predetermined external stimulus.

According to yet another aspect of the invention, a method of monitoring a patient physiological parameter comprises:

providing at least one fiberoptic sensor configured to reflect light at one or more desired wavelengths in response to at least one external stimulus received by the at least one fiberoptic sensor;

configuring the at least one fiberoptic sensor to make physical contact with a patient body;

transmitting a light to the at least one fiberoptic sensor;

measuring a reflected light power level generated by the at least one fiberoptic sensor at each desired wavelength in response to the at least one external stimulus; and determining a change in at least one predetermined patient physiological parameter based on the reflected light power level at each desired wavelength.

DRAWINGS

These and other features, aspects, and advantages of the present invention will become better understood when the following detailed description is read with reference to the accompanying drawings in which like characters represent like parts throughout the drawings, wherein.

While the above-identified drawing figures set forth alternative embodiments, other embodiments of the present invention are also contemplated, as noted in the discussion. In all cases, this disclosure presents illustrated embodiments of the present invention by way of representation and not limitation. Numerous other modifications and embodiments can be devised by those skilled in the art which fall within the scope and spirit of the principles of this invention.

DETAILED DESCRIPTION

Figure 1:
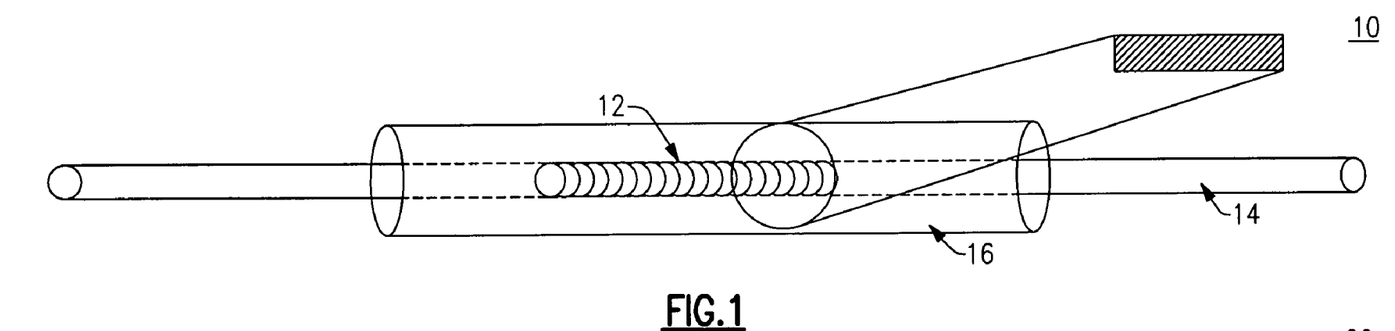
FIG. 1 illustrates a fiber grating micro-strain based physiological sensing element according to one aspect of the invention.

FIG. 1 illustrates a fiber Bragg grating-based, micro-strain based physiological sensing element (fiber optic sensor) 10 according to one aspect of the invention. A fiber Bragg grating is essentially a fiber-optic cable whose core refractive index is periodically modulated. This modulation enables coherent scattering at each refractive index interface, which leads to a constructive resonance at the Bragg wavelength described in further detail below. Fiber optic sensor 10 includes a set of mirror elements, such as, for example, Bragg gratings, 12 that are burned into an optical fiber core 14 using, for example, phase mask and ultra-violet laser inscription techniques. The mirrors 12 are burned in to the optical fiber 14 in such a way that a desired wavelength or range of wavelengths of light transmitted along the optical fiber 14 will be reflected or bounced back toward the input end of the optical fiber 14 by $\lambda=2n\Lambda$, where n is the effective index of refraction in the fiber core, and $\Lambda$ is the periodicity of the grating structure. Other wavelengths of light outside the desired range of wavelengths will pass through the mirror elements 12 toward the output end of the optical fiber 14 without degradation.

Figure 2:
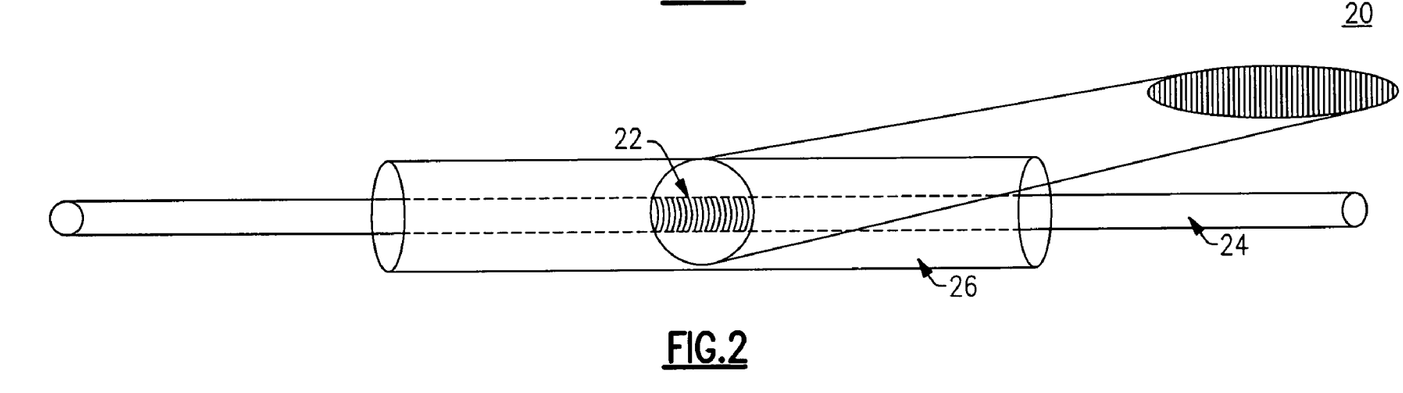
FIG. 2 illustrates a fiber grating mechanical based temperature sensing element according to one aspect of the invention.

The mirror elements 12 can be burned into the optical fiber 14 in a tilted angle such as seen in FIG. 1. This diagonal burning provides an optical sensor 10 that has a higher back propagation of light with less attenuation resulting in an optical sensor 10 having a higher level of efficiency than that achievable using a vertical burning configuration such as seen in FIG. 2. On the other hand, the tilted grating structure enables discrimination of temperature and micro-strain effects by the coupling between the forward and backward propagated guided modes and the coupling between the guided core mode and cladding modes.

Optical fiber 14 is encased in a protective coating 16, such as, without limitation, a polymer, glass fiber, or metalized coating, to provided added mechanical strength, among other features, to the optical fiber 14. The optical fiber 14 has an outer diameter of 125 μm, while the mirror elements (gratings) 12 have an outer diameter of 6-9 μm, and the completed optical sensor 10 including its protective coating 16, has an outer nominal diameter of 250 μm for acrylate coated fiber sensors, and of 150 μm for polyimide and metal coated fiber sensors, according to one embodiment, to achieve a desired level of light propagation associated solely with a desired sensor mode, such as temperature, respiration, pulse, limb acceleration, and so on.

FIG. 2 illustrates a fiber grating mechanical based temperature sensing element (fiber optic sensor) 20, according to another aspect of the invention. Fiber optic sensor 20 is similar in construction to fiber optic sensor 10 shown in FIG. 1; except fiber optic sensor 20 includes a fiber Bragg grating 22 having an apodized structure with vertically aligned mirrors 22 to reflect a desired wavelength or range of wavelengths of light transmitted along the optical fiber 24. Other wavelengths of light outside the desired range of wavelengths will pass through the mirror elements 22 without degradation.

Fiber optic sensor 20 also includes a surface coating 26, constructed from, without limitation, a desired metal or polymer to provide a desired feature such as increased mechanical strength, or a desired enhancement to the sensitivity level of the fiber optic sensor 20.

Figure 3:
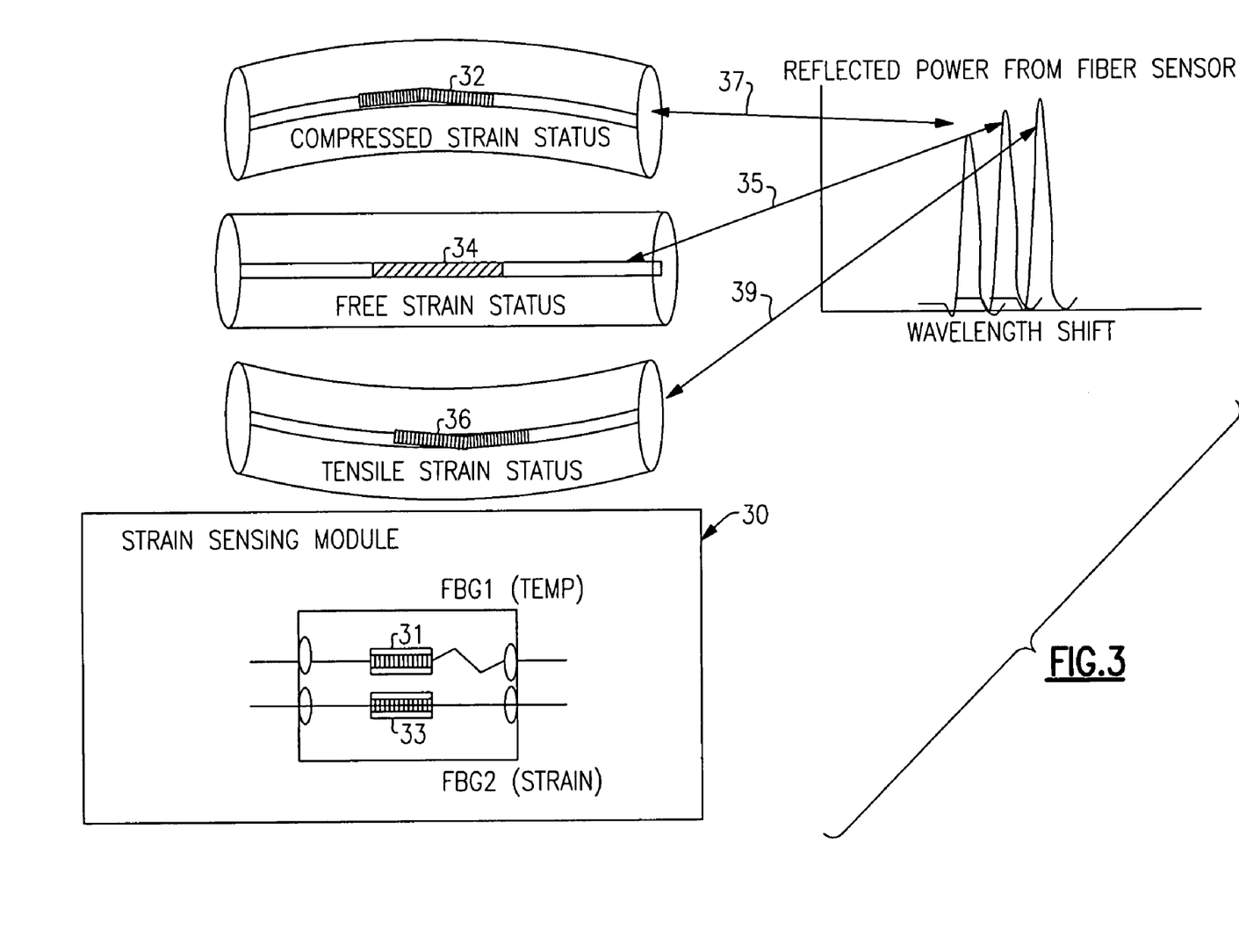
FIG. 3 is a pictorial view illustrating sensing mechanism operation of a fiber optic strain sensing module according to one aspect of the invention.

FIG. 3 is a pictorial view illustrating sensing mechanism operation of a strain sensing module 30, according to one aspect of the invention. Strain sensing module 30 includes both a fiber Bragg grating-based temperature sensing element 31 and a micro-strain based sensing element 33, such as described above with reference to FIGS. 1-2. Here the temperature sensing element is in a strain-free configuration.

Strain sensing module 30 can be operated in a compressed strain state 32, a free strain state 34, or a tensile strain state 36. The free strain state 34 will result in the strain sensing module having a baseline wavelength characteristic 35, such that the module 34 will reflect a predetermined amount of light at a predetermined wavelength. The compressed strain state 32 will result in the strain sensing module having a down-shifted wavelength characteristic 37, such that the module 34 will reflect the same amount of light power at a different predetermined wavelength. The tensile strain state 36 will result in the strain sensing module having an up-shifted wavelength characteristic 39, such that the module 34 will reflect the same amount of light power at a predetermined wavelength that is different from the baseline wavelength characteristic 35 or the shifted wavelength characteristic 37.

Strain sensing module 30 can be calibrated at an ambient temperature simply by subtracting the baseline wavelength shift associated with an unstrained fiber optic temperature sensing element 31 at the ambient temperature from the reflected power associated with a preloaded fiber optic micro-strain based sensing element 33.

Figure 4:
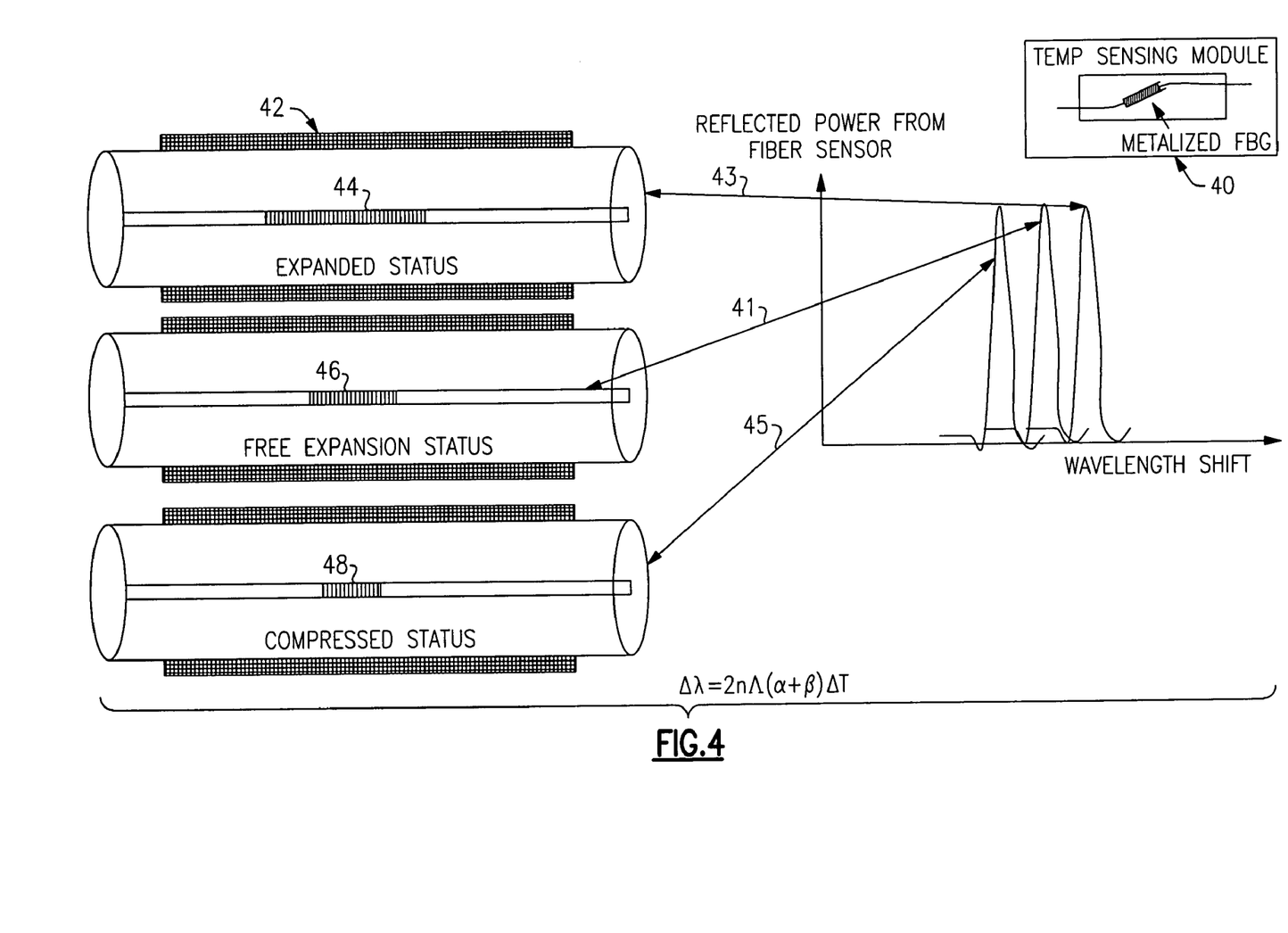
FIG. 4 is a pictorial view illustrating sensing mechanism operation of a fiber optic temperature sensing module according to one aspect of the invention.

FIG. 4 is a pictorial view illustrating sensing mechanism operation of a fiber optic Bragg grating-based temperature sensing module 40 according to another aspect of the invention. Whereas strain sensing module 30 functions in response to sensing element mechanical compression and tensile strain, temperature sensing module 40 functions in response to expansion and compression of the fiber optic sensing element resulting from changes in ambient temperature. The free expansion state 46 that is free from expansion and compression of the fiber optic sensing element produces a baseline wavelength characteristic 41, such that the module 40 will reflect a predetermined amount of light power at a predetermined wavelength. The expanded state 44 that results from expansion of the fiber optic sensing element produces an up-shifted wavelength characteristic 43, such that the module 40 will reflect the same amount of light power at a different predetermined wavelength. The compressed state 45 that results from compression of the fiber optic sensing element, produces a down-shifted wavelength characteristic 45, such that the module 40 will reflect the same amount of light at a predetermined wavelength that is different from the baseline wavelength characteristic 41 or the shifted wavelength characteristic 43.

Fiber optic Bragg grating-based temperature sensing module 40 exhibits a wavelength shift according to one aspect of the invention that is defined by a relationship represented as $\lambda = 2n\Lambda(\beta+\alpha)$ T, where $\Lambda$ is the periodicity of the grating structure, T is absolute temperature, $\beta$ is a thermo-optic coefficient equal to about $8 \times 10^{-6}$ $1/^\circ$ C. and $\alpha$ is a thermal expansion coefficient equal to about $23 \times 10^{-6}$ $1/^\circ$ C. with a 500 nm thick Al metalized surface 42.

Figure 5:
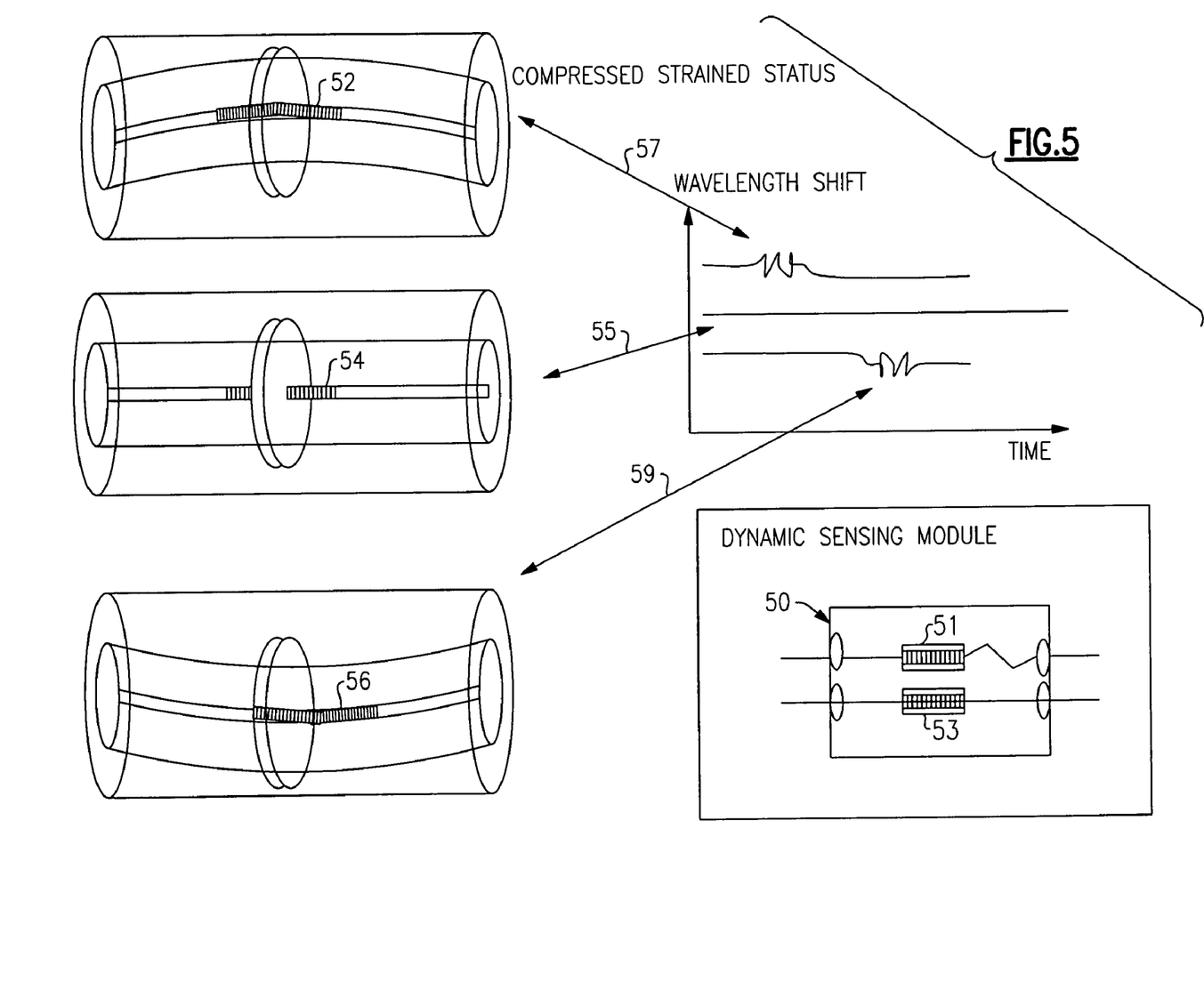
FIG. 5 illustrates a fiber grating loading based physiological sensing module according to one aspect of the invention.

FIG. 5 illustrates a fiber optic dynamic sensing module 50 that includes a fiber Bragg grating loading-based physiological sensing mechanism according to one aspect of the invention. The sensing mechanism includes both a Bragg grating-based fiber optic temperature sensing element 51 and a fiber optic vibration/acceleration micro-strain based sensing element 53. Although similar to the strain sensing module 30, dynamic sensing module 50 is also responsive to bending moments associated with the vibration/acceleration micro-strain based sensing element 53.

Fiber optic vibration/acceleration micro-strain based sensing element 53 can operate in a compressed strain state 52, a free vibration state 54, or a tensile strain state 56. The free vibration state 54 will result in the dynamic sensing module 50 having a wavelength shift with very small standard deviation characteristic 55, such that the module 50 will simply respond to environmental temperature variations without exhibiting vibration characteristics. The compressed strain state 52 will result in the dynamic sensing module 50 having a down-shifted wavelength characteristic 57, such that the module 50 will reflect a predetermined amount of light power within a range of predetermined wavelengths. The tensile strain state 56 will result in the dynamic sensing module 50 having an up-shifted wavelength characteristic 59, such that the module 50 will reflect the same amount of light power within a predetermined range of wavelengths that is different from the down-shifted wavelength characteristic 57.

Dynamic sensing module 50 can be calibrated at an ambient temperature simply by subtracting the baseline wavelength shift associated with an unstrained fiber optic temperature sensing element 51 at the ambient temperature from the baseline wavelength shift associated with a preloaded fiber optic vibration/acceleration micro-strain based sensing element 53.

Figure 6:
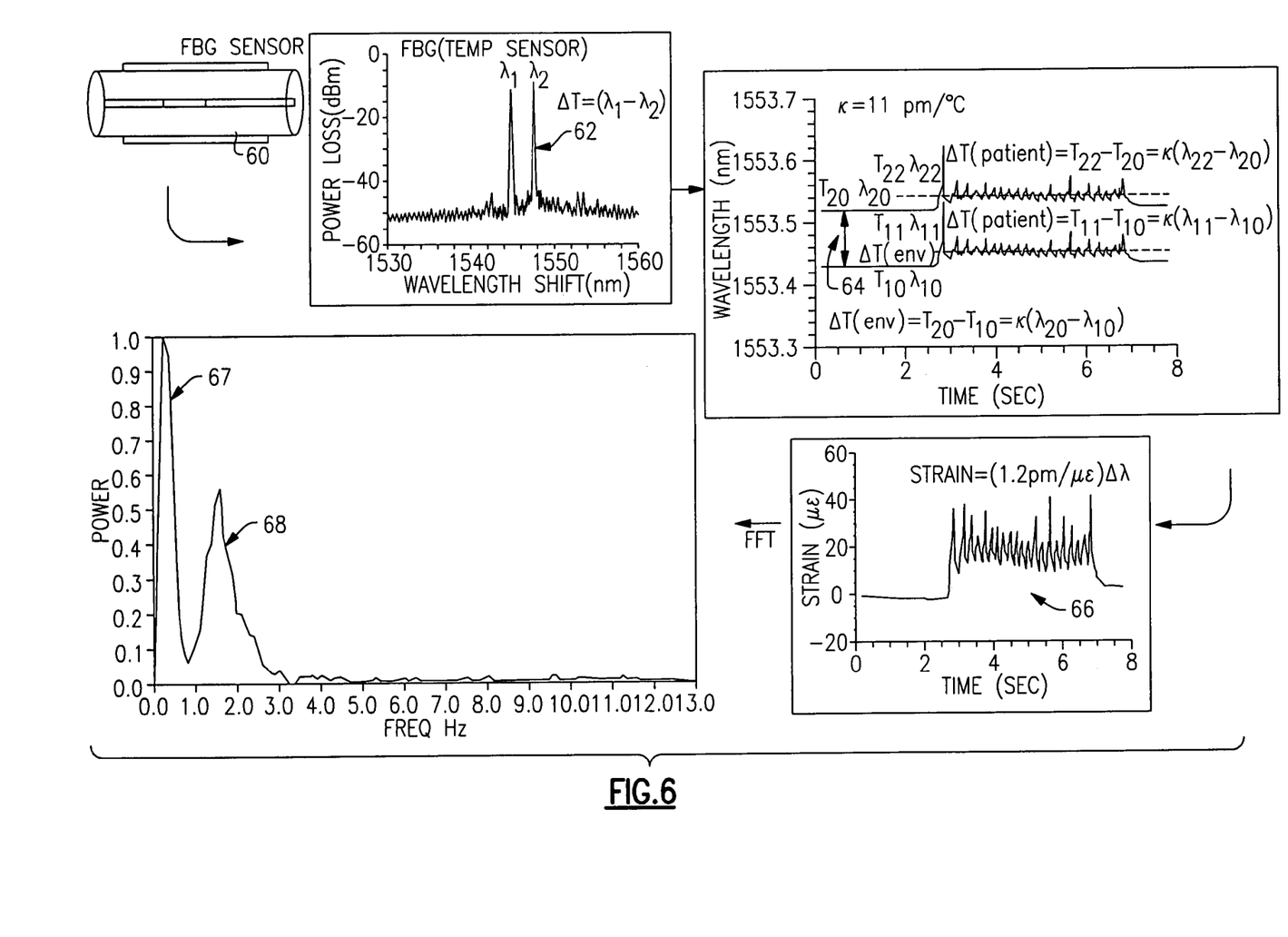
FIG. 6 is a pictorial diagram illustrating physiological parameter sensing principles according to one aspect of the invention.

FIG. 6 is a pictorial diagram illustrating physiological parameter sensing principles according to one aspect of the invention. Physiological parameters described in more detail below are monitored according to one embodiment via a fiber Bragg grating based sensor 60. Sensor 60 operates according to one aspect, to alter the light power reflected by the sensor 60 in response to the sensor 60 wavelength shift 62 that is determined by the changing physiological parameter, e.g. temperature and strain, being monitored.

A change, for example, in patient temperature 64 is monitored over time in response to the sensor 60 wavelength shift caused by the shift in temperature. Physiological activity 66 is also monitored over time in response to the sensor 60 wavelength shift caused by the physiological activity such as, without limitation, metabolic activity or limb displacement. The foregoing temperature and strain measurement data are then transformed into a corresponding heart beat rate 67 and a corresponding respiration rate 68.

Figure 7:
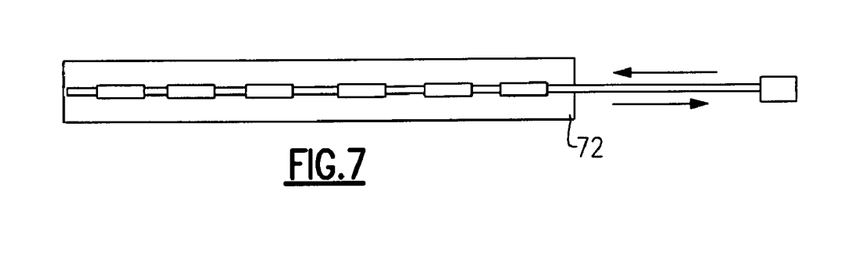
FIG. 7 illustrates a fiberoptic physiological sensing module according to one aspect of the invention.

FIGS. 7-10 illustrate fiberoptic physiological sensing modules according to various aspects of the invention. FIG. 7, for example, depicts a fiberoptic sensing belt type module 72 that includes a plurality of fiber optic sensors such as those described above with reference to FIGS. 1-5.

Figure 8:
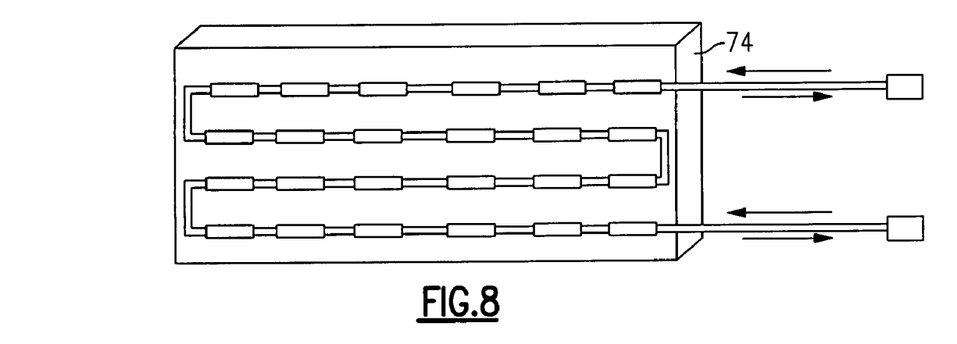
FIG. 8 illustrates a fiberoptic physiological sensing module according to another aspect of the invention.

FIG. 8 illustrates a fiberoptic physiological sensing module 74 according to another aspect of the invention. Sensing module 74 includes a plurality of fiber optic sensors such as those described above with reference to FIGS. 1-5, in which the fiber optic sensors are arranged in a matrix pattern.

Figure 9:
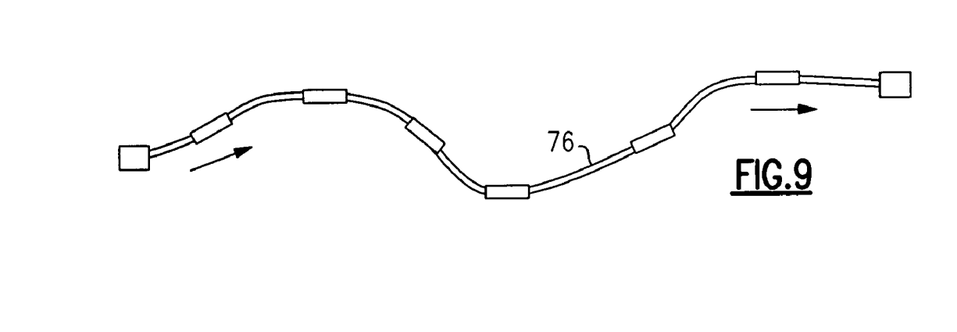
FIG. 9 illustrates a fiberoptic physiological sensing module according to yet another aspect of the invention.

FIG. 9 illustrates a fiberoptic physiological sensing module 76 according to yet another aspect of the invention. Sensing module 76 includes a plurality of fiber optic sensors such as those described above with reference to FIGS. 1-5, in which the fiber optic sensors are integrated along a fiberoptic sensing cable type catheter.

Figure 10:
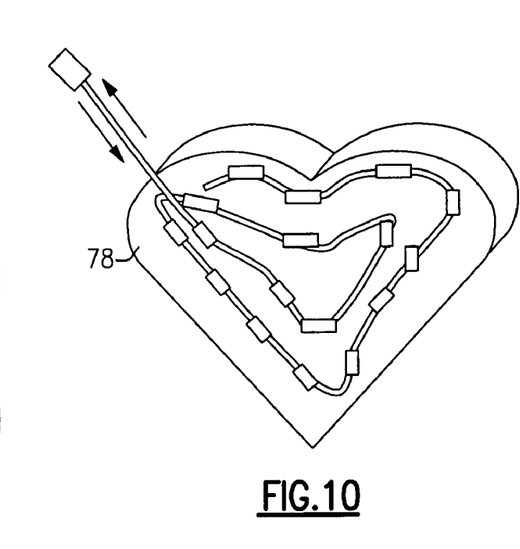
FIG. 10 illustrates a fiberoptic physiological sensing module according to still another aspect of the invention.

FIG. 10 illustrates a fiberoptic physiological sensing module 78 according to still another aspect of the invention. Sensing module 78 includes a plurality of fiber optic sensors such as those described above with reference to FIGS. 1-5, in which the fiber optic sensors are disposed within a fiberoptic sensing patch pad.

Figure 11:
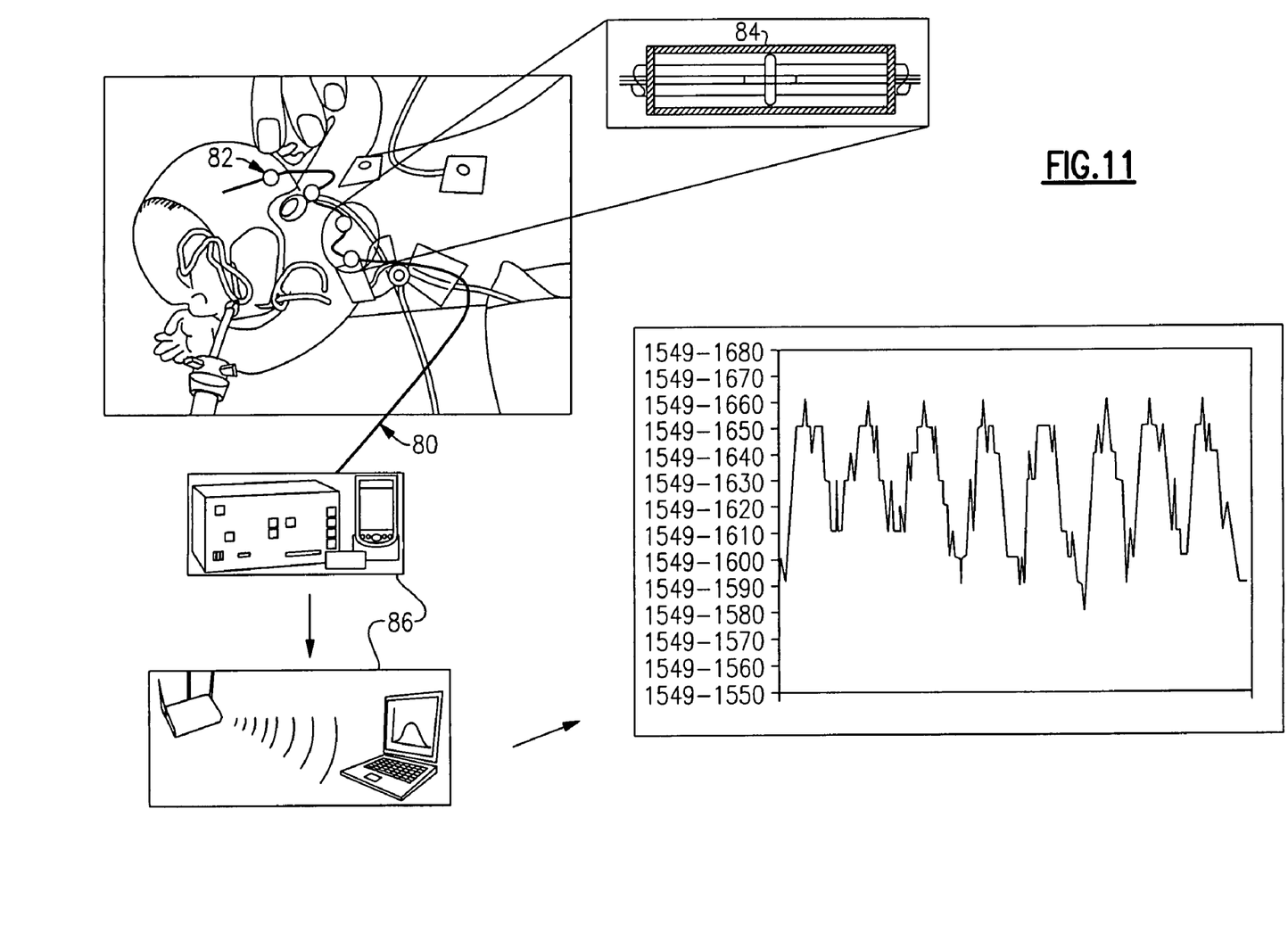
FIG. 11 illustrates application of a fiberoptic physiological accelerometer module according to one aspect of the invention.

FIG. 11 illustrates application of a fiberoptic physiological accelerometer 84 according to one aspect of the invention. The fiberoptic physiological sensing module 84 forms one portion of a fiberoptic surface temperature, acceleration system 80 that includes a plurality of individual sensor nodes 82. Fiberoptic surface temperature, acceleration system 80 functions to monitor, without limitation, chest wall expansion-respiration, chest wall expansion-heart rate, metabolic activity-temperature, limb displacement-activity, energy use, and transcutaneous $O_2$-blood/gas information. Differential measurement from such a sensing module that integrates both temperature sensor and an accelerometer provides both body temperature of a patient and dynamic strain that is associated with one of physiological activities, such as chest wall expansion-respiration.

The fiberoptic physiological accelerometer 84 may include one or more fiber optic dynamic sensing modules 50 such as described above with reference to FIG. 5, and consists of a seismic mass supported by a fiber. Micro-strain imparted by patient motion induces a wavelength shift that is detectable by an interrogation system 86. Interrogation system 86 monitors the wavelength shift and transmits a wireless signal that is received remotely via a computer that employs software to distinguish different patient physiological parameters.

Figure 12:
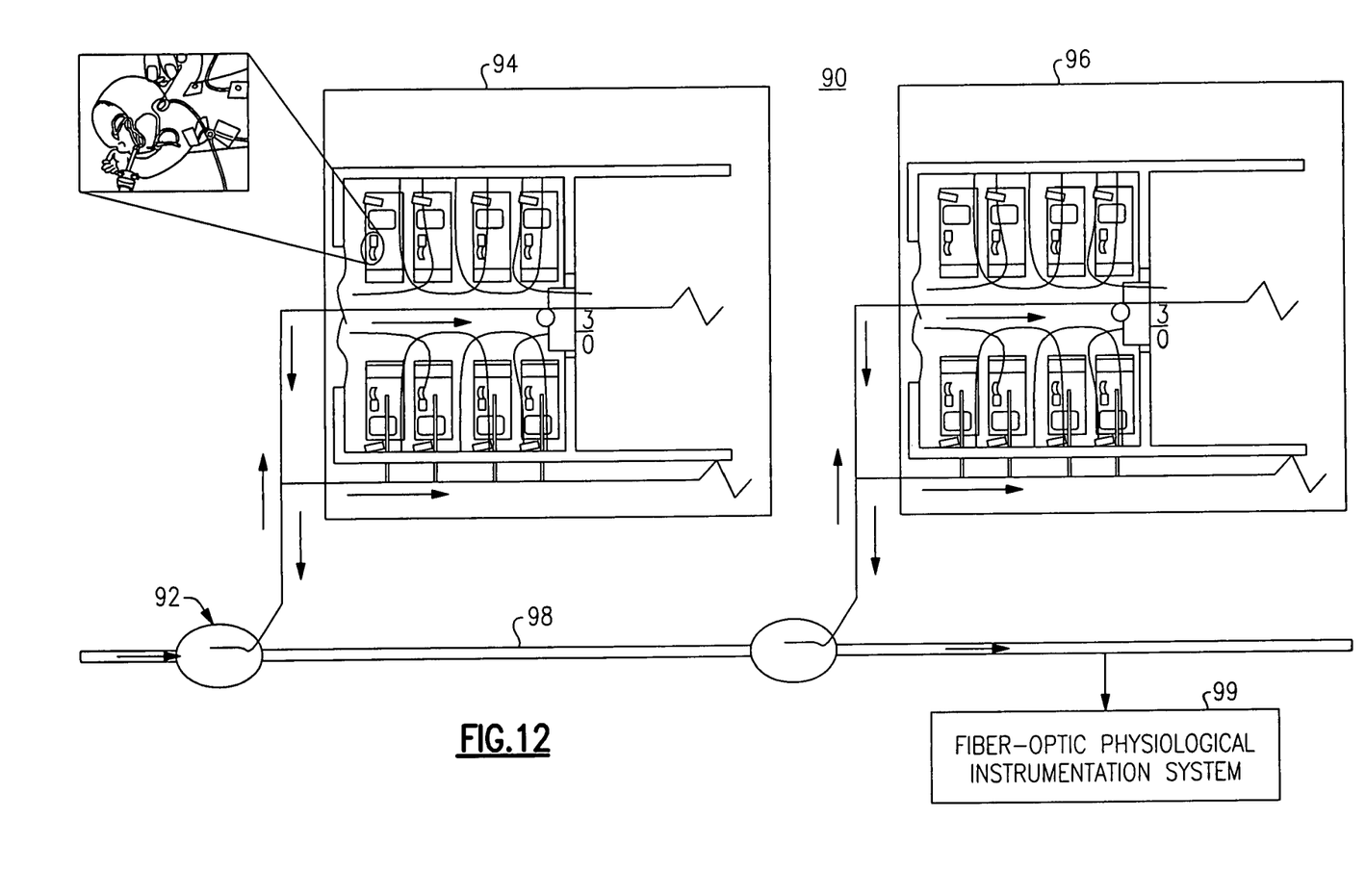
FIG. 12 illustrates a fiberoptic physiological instrumentation system according to one aspect of the invention.

FIG. 12 illustrates a fiberoptic physiological instrumentation system 90 according to one aspect of the invention. Fiberoptic physiological instrumentation system 90 includes a plurality of in hospital baby care facilities 94, 96. Each in hospital baby care facility 94, 96 includes a plurality of fiberoptic physiological modules 84 such as described above with reference to FIG. 11. All of the fiberoptic physiological modules 84 are coupled together along an optical fiber 98 via a plurality of optical couplers 92. The optical fiber 98 is coupled to a fiber-optic physiological instrumentation system 99 that may include a computer or other suitable means that employs software to distinguish different patient physiological parameters.

Fiberoptic physiological instrumentation system 90 advantageously employs an architecture that significantly reduces the overall system costs generally associated with more conventional physiological instrumentation systems that are not so easily integrated together into a single, non-redundant hardware/software system.

Figure 13:
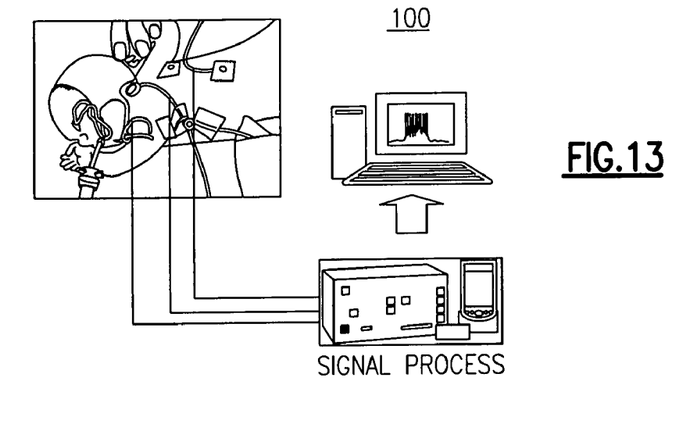
FIG. 13 illustrates a single baby physiological parameter monitoring biomedical system, according to one aspect of the invention.

FIG. 13 illustrates a single baby physiological parameter monitoring biomedical system 100, according to one aspect of the invention. System 100 can be implemented, without limitation, the same as, or similar to, the fiberoptic physiological accelerometer module 84 described above with reference to FIG. 11.

Figure 14:
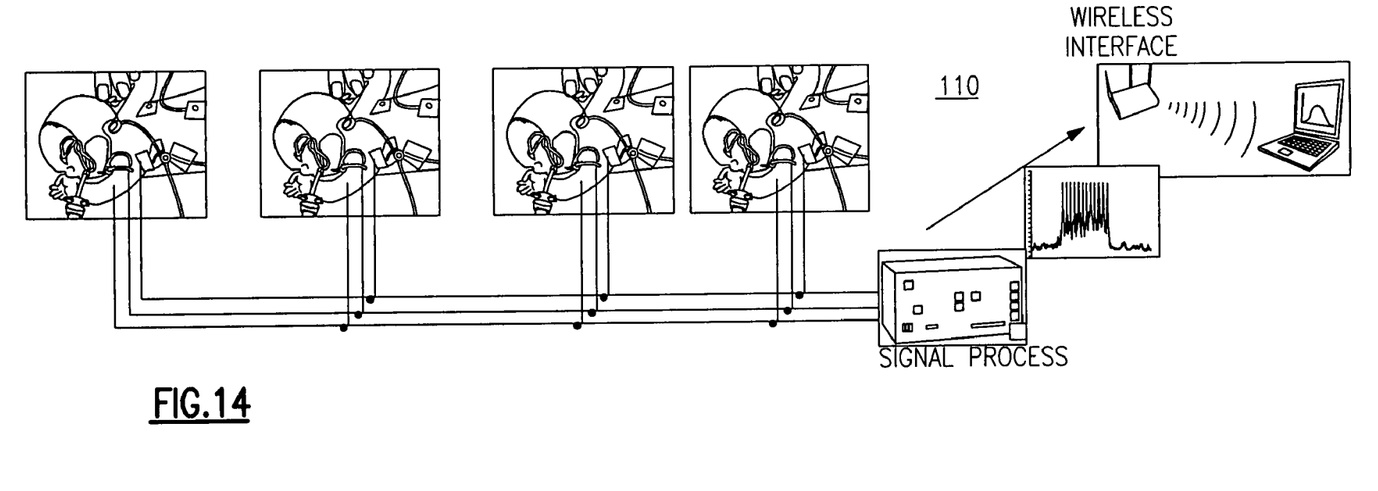
FIG. 14 illustrates a multi baby physiological parameter monitoring biomedical system, according to one aspect of the invention.

FIG. 14 illustrates a multi baby physiological parameter monitoring biomedical system 110, according to one aspect of the invention. The multi baby physiological parameter monitoring biomedical system 110 employs a plurality of single baby physiological parameter monitor biomedical system 100, such as depicted in FIGS. 11 and 13. The multi baby physiological parameter monitoring biomedical system 110 is scalable such that it is capable of meeting the needs of a particular facility or environment. System 110 is capable of monitoring physiological parameters associated with a single patient, or can be expanded with little or no additional hardware/software expenditure(s), to monitor thousands of patients using a single signal processing interface.

Figure 15:
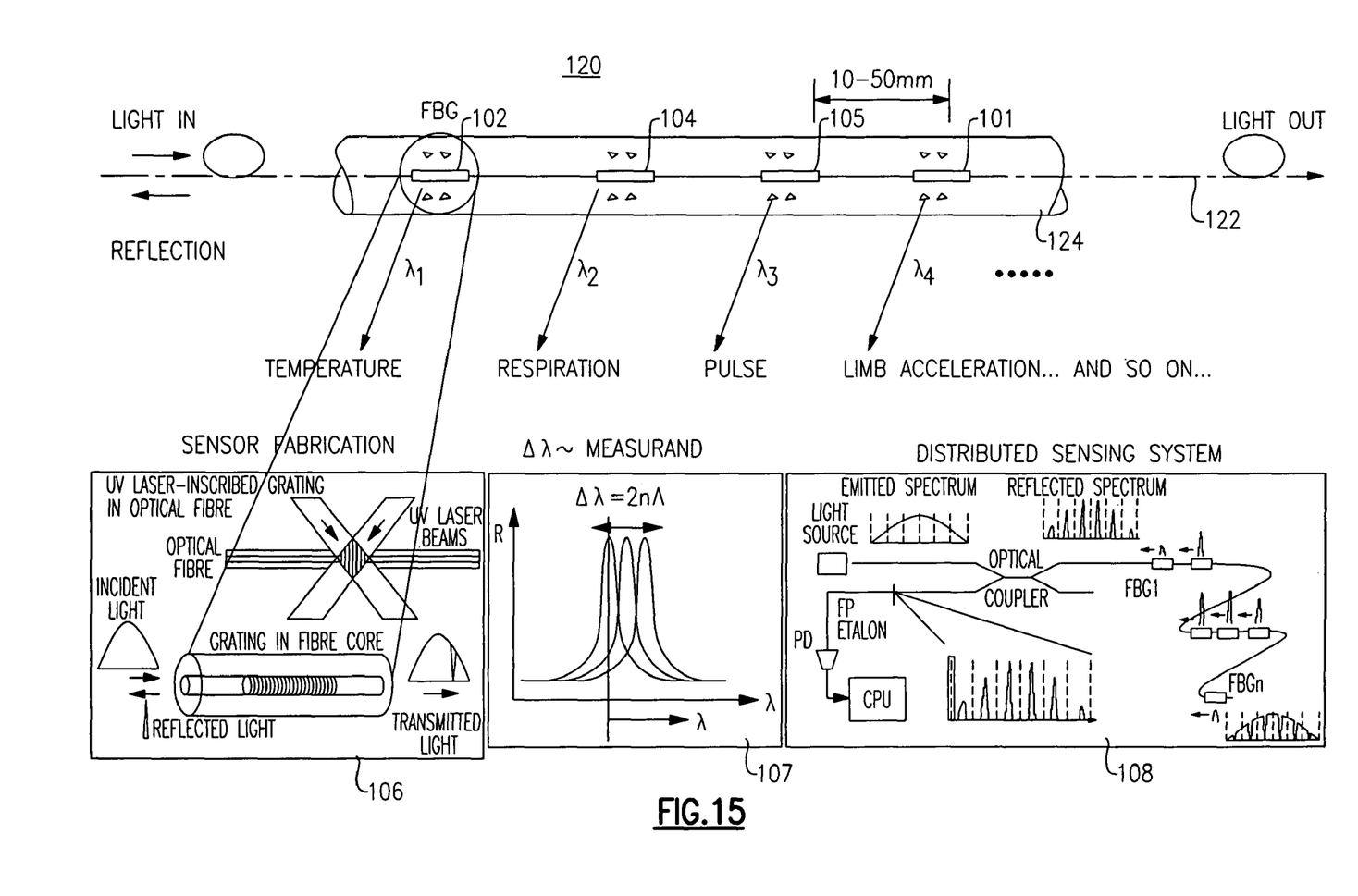
FIG. 15 illustrates a physiological multi-parameter fiber optic sensing system according to one aspect of the invention.

FIG. 15 illustrates a physiological multi-parameter fiber optic sensor module 120 according to another aspect of the invention. Fiber optic sensor module 120 has a fiber optic temperature sensing sensor 102, a fiber optic respiration sensor 104, a fiber optic pulse sensor 105 and a fiber optic limb acceleration sensor 101, among others, integrated along the length of an optical fiber 122. Optical fiber is covered with a protective shroud 124, such as described herein before to provide added tensile or mechanical strength and to protect the fiber optic sensors 101, 102, 104, 105 and optical fiber 122 from environmental damage.

Each fiber optic sensor 101, 102, 104, 105 comprises a diffraction grating 106 such as a fiber Bragg grating (FBG) that is burned into the optical fiber in a manner to achieve a desired level of reflected light power at a desired light wavelength passing through the corresponding fiber optic sensor. The reflected light power associated with a particular sensor 101, 102, 104, 105 is dependent upon a shift in its corresponding wavelength 107 in response to a desired patient physiological variable.

This wavelength shift 107 is monitored via a distributed sensing system 108 that includes a broadband light source such as tunable laser, light-emitting diode and superluminescent lamp, optical coupler, Fabry-Perot (FP) etalon, photodetector (PD), a personal computer (PC), digital signal processor (DSP), or any suitable signal processing means to transform a reflected level of light power at a corresponding wavelength into the desired corresponding patient physiological variable measurement data. The fiberoptic sensors, such as fiber Bragg grating (FBG), could be from FBG1 to FBGn, potentially distributed in a large facility, such as a hospital.

In summary explanation, a fiberoptic patient health multi-parameter monitoring system including one or more fiberoptic sensors or sensing modules has been described. The fiberoptic monitoring system and its associated sensor(s) are capable of providing continuous, real-time monitoring or airborne and waterborne pathogens in microenvironments and ambient environments. The fiberoptic monitoring system and its associated sensor(s) are able to characterize a microenvironment temperature and humidity across a larger volume of the microenvironment than that which is presently achievable using known monitoring systems, for closed loop temperature control through distributed sensors.

The fiberoptic sensors described herein can be advantageously configured in a sensor array to reduce the cost associated with the instrumentation required to support each sensor through wavelength division multiplexing (WDM). Further, the fiberoptic sensors described herein advantageously provide secure and reliable operation in environments where use of conductive, traditional electronic sensor are highly undesirable and contribute to degradation of sensor signals due to electromagnetic interference.

Further, the fiber optic sensors described herein advantageously provide improved wearability and usability of sensors associated with patient health including, without limitation, respiration, heart rate, body motion, blood analytes, temperature, electrical activity on body surface, pressure, ultrasound, and cardiac output. The fiberoptic sensors described herein have sufficiently small diameters, for example, to permit real-time, continuous monitoring in an indwelling catheter in a neonate significantly below gestational age.

Other advantages provided by the fiber optic sensors described herein include utilization of a biocompatible material to support invasive procedures or to support sensor fidelity in aqueous environments. The fiber optic sensors described herein advantageously allow a configuration that employs a single optical fiber or multiple braids, depending upon the need for sensor redundancy or level of sensor density per length of fiber.

The features provided by the fiber optic sensors described above allow for use of a portable interrogator and sensor system for new telemetry applications, where desirable or necessary. The size, structure and operational features of the fiber optic sensors described herein further advantageously provide modular functionality, diversity, and flexible functionality with different sensor fibers through a plug and play fiber sensor swap capability In further summary explanation, a physiological sensing platform described herein works through the utilization of a plurality of diffraction gratings, such as Bragg gratings, located along the length of an optical fiber, as described herein above. The purpose of each grating is to reflect forward propagating light back down the fiber in the direction from which it came. As the spectrum of this light is evaluated, the light that has been reflected now contains a spectral signature corresponding to each individual grating along the fiber length. At the site of each grating, either the fiber core or cladding has been significantly modified so that the effective refractive index of the grating structure changes in tandem with a specific external stimulus, such as, without limitation, temperature, pressure, or motion. The change in refractive index results in a corresponding wavelength and intensity shift of the spectral signature associated with each grating. Thus, as light propagates down the fiber and is reflected, the external stimulus can also be monitored.

The fiberoptic patient multi-parameter monitor devices and system described herein according to different aspects of the invention provide numerous advantages over know monitoring devices and systems. The slenderness of the optical fiber, i.e. 14, 24 employed in the embodiments described above, for example, allows for the possibility of being woven into a garment that can be worn, reducing the sensor's presence in the immediate patient environment. Further, since the optical sensor is optical in nature and closely bound to the patient, the device will not be as dependent upon the interface between the sensor and skin, improving the chances of a proper sensor readout.

The fiberoptic patient multi-parameter monitor devices and system described herein also advantageously circumvent the potentially harsh electrical environment of a patient care area, especially in the presence of electrocautery, defibrillation, or MRI equipment, since the silica-based material of the fiber is generally non-conductive at the operating frequency of the interfering devices.

The fiberoptic patient multi-parameter monitor devices and system described herein also employ a silica-based optical fiber material that is resistant to fluids. This silica-based material of the optical fiber is generally biologically inert, unless treated to respond as described for particular embodiments described above.

Several additional advantages provided by the fiberoptic patient multi-parameter monitor devices and system described herein are directed to, without limitation, cable tethering, sensor swapping capabilities, scalability, and novel parameter measurement capabilities. Patient monitors, as commonly known and employed in hospitals today, usually have at least one cable associated with each sensor. In a high acuity care environment, for example, 10 ECG sensors are used for heart activity monitoring, 1 sensor is used for surface temperature monitoring, and 1 sensor is used for blood oxygen saturation monitoring, already resulting in 12 cables hanging from a patient. The fiberoptic devices and system described above advantageously employ a single cable, regardless of the type and number of fiberoptic sensors involved.

Because the reflected light associated with each fiberoptic sensor occupies a small slice of the total optical spectrum used in the fiberoptic patient multi-parameter monitoring system described herein, fiberoptic patient multi-parameter monitoring devices and systems can be designed to accommodate several hundreds to thousands of sensors by spacing the spectrum of each sensor appropriately within the allotted band. This technique is also known as wavelength division multiplexing, as stated herein before. If used in monitoring microenvironments, one sensor system can provide broad sensor coverage for an entire ward or hospital, thus reducing instrumentation costs for the hospital. Further, at least one sensor diffraction grating may be configured to function in association with a different sensor grating such that together the at least one diffraction grating and for expected artifacts including signal drift.

The present inventors recognized that the nature of fiberoptic sensing in combination with the properties of microbial pathogens or biomolecules enables spatially distributed, remote sensing of their presence or absence. A fiber sensor can be treated, for example, to bind to a pathogen or biomolecule of interest. In neonatal microenvironments, the humidity is generally much higher than that of the outside ambient environment to maintain skin pliability. This is also a breeding ground for microbes which can seriously compromise the health of a neonate, whose immune systems are far from developed. Sensing the presence or absence of microbial pathogens or biomolecules can be implemented, for example, by treating the cladding or core of the grating sensor with a marker which specifically binds to the microbe of interest. The adherence of the pathogen to the grating modifies the effective refractive index of the grating structure and subsequently changes the wavelength of the reflected light.

According to another embodiment, four fiberoptic physiological sensor modules are integrated into a mattress or blanket for noninvasively monitoring the temperature, respiration rate, heart rate, and overall infant body motion. Either single-point or distributed plug-and-play sensing modules are installed into the sensing system with a single optical interrogator evaluating the interaction between sensors and the external environment, which is fully immune to electromagnetic RF radiation typically encountered in the medical setting.

Another benefit of a fiber optic sensor implemented according to the principles described herein is the ability to functionalize the outer cladding of the periodic grating structure to be responsive to the phenomena of interest, as stated herein before. Monitoring using the fiber optic grating involves transducing the phenomena of interest into an optically observable effect by either modulating the periodic spacing of the grating, or by modulating the effective refractive index of the entire grating structure. Thus, any parameter of interest can be observed provided the phenomena can be transduced into either a mechanical displacement or dielectric change, and provided that sufficient isolation between other external influences that create the same effect are incorporated.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A fiberoptic patient health multi-parameter monitoring system, comprising:
   an optical sensing fiber cable comprising a plurality of predetermined sensing modules; and
   each sensing module comprising at least one diffraction grating having a corresponding resonant wavelength that shifts in response to predetermined external stimuli to provide spectral signatures corresponding to patient physiological parameters such that a plurality of dynamically changing patient physiological parameters are simultaneously represented by the spectral signatures associated with the plurality of predetermined sensing modules,
   each sensing module further comprising at least one fiber optic ambient temperature calibration element exhibiting a baseline wavelength shift at ambient temperature, wherein at least one diffraction grating within the sensing module is a calibrated diffraction grating based on the baseline wavelength shift of a corresponding ambient temperature calibration element within the sensing module.

2. The fiberoptic patient health multi-parameter monitoring system according to claim 1, wherein the plurality of diffraction gratings comprises an apodized Bragg grating.

3. The fiberoptic patient health multi-parameter monitoring system according to claim 1, wherein the predetermined external stimuli are selected from temperature, heart beat induced pressure variation, and physical displacements.

4. The fiberoptic patient health multi-parameter monitoring system according to claim 1, wherein the optical sensing fiber cable and the plurality of sensing modules are further configured together to detect external stimuli induced wavelength shifts along the optical sensing fiber cable.

5. The fiberoptic patient health multi-parameter monitoring system according to claim 4, wherein the external stimuli induced wavelength shift comprises a spectral signature corresponding to dynamic response in both amplitude and frequency characteristics.

6. The fiberoptic patient health multi-parameter monitoring system according to claim 4, further comprising a plurality of different types of optical sensing fiber cables disposed at different locations surrounding a patient, wherein each fiber sensing cable corresponds to a particular type of sensing module.

7. The fiberoptic patient health multi-parameter monitoring system according to claim 1, wherein each diffraction grating has a length between about 3 mm and about 20 mm, and further has a diameter between about 6 microns and about 10 microns.

8. The fiberoptic patient health multi-parameter monitoring system according to claim 1, wherein the optical sensing fiber cable and the plurality of diffraction gratings comprise a silica-based biocompatible material that is substantially non-conductive at the operating frequency of electrocautery, defibrillation, and magnetic resonance imaging equipment.

9. The fiberoptic patient health multi-parameter monitoring system according to claim 1, wherein the optical fiber sensing cable and the plurality of diffraction gratings comprise a silica-based biologically inert material that is highly resistant to weak acids, bases, water, and human body fluids.

10. The fiberoptic patient health multi-parameter monitoring system according to claim 1, wherein the optical fiber sensing cable and the plurality of diffraction gratings together comprise a functionalized cladding that is sensitive to predetermined external stimuli.

11. The fiberoptic patient health multi-parameter monitoring system according to claim 1, wherein the optical fiber sensing cable and the plurality of sensing modules together are modular such that the fiberoptic monitoring system accommodates a plurality of different types of sensing modules in communication with a single multi-channel signal interrogator.

12. The fiberoptic patient health multi-parameter monitoring system according to claim 1, further configured to monitor patient health parameters selected from respiration, heart rate, body motion, blood analytes, temperature, thermal profile, electrical activity on the surface of the patient body, heart beat induced pressure variation, ultrasound, and cardiac output.

13. The fiberoptic patient health multi-parameter monitoring system according to claim 1, wherein the fiber optic monitoring system is further configured as a distributed sensor array across a predetermined microenvironment or ambient environment.

14. The fiberoptic monitoring system according to claim 1, wherein the at least one optical fiber or fiber braid is encapsulated in a thin film of material to improve the coefficient of thermal expansion of the at least one diffraction grating.

15. The fiberoptic monitoring system according to claim 14, wherein the thin film of material is applied to the at least one optical fiber or fiber braid to improve the sensitivity of the at least one diffraction grating to vibration, strain, and motion.

16. The fiberoptic patient health multi-parameter monitoring system according to claim 1, wherein at least one predetermined diffraction grating is configured to function in association with a different grating such that together the at least one predetermined diffraction grating and the different grating together compensate for expected signal drifts.

17. The fiberoptic patient health multi-parameter monitoring system according to claim 1, further comprising an interrogator configured to determine patient health parameters selected from respiration, heart rate, body motion, blood analytes, temperature, electrical activity on the surface of the patient body, pressure, ultrasound, and cardiac output in response to the changes in either the effective refractive index or the grating periodicity of at least one diffraction grating.

18. The fiberoptic patient health multi-parameter monitoring system according to claim 1, wherein the optical fiber sensing cable is configured to make physical contact with a patient body such that the at least one predetermined external stimulus is provided by a patient physiological parameter.

19. The fiberoptic patient health multi-parameter monitoring system according to claim 1, wherein the optical fiber sensing cable is attached to an article of clothing or blanket which facilitates maintenance of physical contact between the optical fiber sensing cable and a patient body.

20. The fiberoptic patient health multi-parameter monitoring system according to claim 1, wherein the plurality of diffraction gratings comprises an apodized tilted grating.

* * * * *